US012575762B2

(12) United States Patent
Hashimoto et al.

(10) Patent No.: US 12,575,762 B2
(45) Date of Patent: Mar. 17, 2026

(54) WEARABLE SENSOR AND SWEATING ANALYSIS DEVICE

(71) Applicant: NTT, Inc., Tokyo (JP)

(72) Inventors: Yuki Hashimoto, Tokyo (JP); Kei Kuwabara, Tokyo (JP); Hiroyoshi Togo, Tokyo (JP)

(73) Assignee: NTT, INC., Tokyo (JP)

( * ) Notice: Subject to any disclaimer, the term of this patent is extended or adjusted under 35 U.S.C. 154(b) by 1224 days.

(21) Appl. No.: 17/431,018

(22) PCT Filed: Mar. 25, 2020

(86) PCT No.: PCT/JP2020/013241
§ 371 (c)(1),
(2) Date: Aug. 13, 2021

(87) PCT Pub. No.: WO2020/209061
PCT Pub. Date: Oct. 15, 2020

(65) Prior Publication Data
US 2022/0054053 A1 Feb. 24, 2022

(30) Foreign Application Priority Data

Apr. 8, 2019 (JP) .................................. 2019-073297

(51) Int. Cl.
*A61B 10/00* (2006.01)
*A61B 5/145* (2006.01)
*A61B 5/1477* (2006.01)

(52) U.S. Cl.
CPC ........ *A61B 5/14521* (2013.01); *A61B 5/1477* (2013.01); *A61B 10/0064* (2013.01)

(58) Field of Classification Search
CPC .............. A61B 5/14521; A61B 5/1477; A61B 10/0064; A61B 5/14517; A61B 5/4266; G01N 27/00; G01N 33/50
See application file for complete search history.

(56) References Cited

U.S. PATENT DOCUMENTS 6,045,541 A * 4/2000 Matsumoto .......... A61B 5/4881
604/289
7,037,277 B1 * 5/2006 Smith ................ A61B 5/14514
600/584
(Continued)

FOREIGN PATENT DOCUMENTS

CN 108169307 A 6/2018
JP H10221221 A 8/1998
(Continued)

OTHER PUBLICATIONS

Gao et al. "Fully integrated wearable sensor arrays for multiplexed in situ perspiration analysis," Macmillan Publishers Limited, Jan. 28, 2016, vol. 529, pp. 509-526.

*Primary Examiner* — Jacqueline Cheng
*Assistant Examiner* — Tho Q Tran
(74) *Attorney, Agent, or Firm* — Slater Matsil, LLP

(57) ABSTRACT

A wearable sensor includes: a base member which is worn on a body of a wearer; a hole-like flow passage which penetrates through the base member; a sensor part which detects a signal as to electrical characteristics of a solution inside the flow passage; and a heater which is located in the base member in such a way as to enclose the flow passage.

20 Claims, 6 Drawing Sheets

(56)                    References Cited

U.S. PATENT DOCUMENTS

| | | | | |
|---|---|---|---|---|
| 7,931,592 | B2 * | 4/2011 | Currie ................ | A61B 5/14546 |
| | | | | 600/309 |
| 10,004,434 | B1 * | 6/2018 | Paranjape .......... | A61B 5/14514 |
| 2017/0119289 | A1 | 5/2017 | Yoshioka et al. | |
| 2017/0354808 | A1 * | 12/2017 | Heikenfeld .......... | A61B 5/1451 |
| 2018/0020966 | A1 * | 1/2018 | Begtrup ................... | A61B 5/01 |
| | | | | 600/301 |
| 2018/0095067 | A1 * | 4/2018 | Huff ................. | G01N 33/48721 |
| 2018/0199866 | A1 * | 7/2018 | Heikenfeld ........ | A61B 5/14521 |
| 2018/0289296 | A1 | 10/2018 | Heikenfeld et al. | |
| 2019/0082999 | A1 * | 3/2019 | Heikenfeld .......... | A61B 5/7221 |
| 2020/0367819 | A1 | 11/2020 | Aizawa | |

FOREIGN PATENT DOCUMENTS

| | | | | | |
|---|---|---|---|---|---|
| JP | 2013500492 | A | * | 1/2013 | |
| JP | 2015158393 | A | | 9/2015 | |
| JP | 2017080245 | A | | 5/2017 | |
| JP | 3212682 | U | | 9/2017 | |
| JP | 2017198577 | A | | 11/2017 | |
| KR | 20180131178 | A | | 12/2018 | |
| WO | WO-2007114794 | A1 | * | 10/2007 | ........ B01L 3/502792 |
| WO | 2019031256 | A1 | | 2/2019 | |

* cited by examiner

WEARABLE SENSOR AND SWEATING ANALYSIS DEVICE

CROSS-REFERENCE TO RELATED APPLICATIONS

This application is a national phase entry of PCT Application No. PCT/JP2020/013241, filed on Mar. 25, 2020, which claims priority to Japanese Application No. 2019-073297, filed on Apr. 8, 2019, which applications are hereby incorporated herein by reference.

TECHNICAL FIELD

Embodiments of the present invention relates to a wearable sensor and a perspiration analysis device for analyzing components in human perspiration.

BACKGROUND

A human body has tissues, such as muscles and nerves, which conduct electrical activity, and in order to cause these tissues to continuously normally operate, the human body is provided with a mechanism, which keeps an electrolytic concentration in the body constant, mainly by functions of an autonomic nervous system and an endocrine system. For example, when a large amount of an electrolyte in the body is lost by perspiration caused by exposure to a hot environment for a long time, excessive exercise, and the like and a value of the electrolytic concentration in the body becomes out of a normal value, a variety of symptoms typified by heatstroke are caused.

In recent years, due to these circumstances, a study to comprehend electrolyte abnormality of the human body by monitoring the electrolytic concentration in the perspiration has been conducted. For example, in Non-Patent Literature 1, a wearable device which monitors an electrolyte ion concentration in the perspiration has been proposed, and it has been becoming clear from a measurement result obtained by this device that the electrolyte ion concentration is useful as a biomarker for dehydration.

When it is considered that the electrolytic concentration in the perspiration is continuously measured for a long time in a form in which the device is worn on a human body, for example, in a case where intense exercise is conducted for a given time; thereafter, resting is made; and exercise is conducted again, that is, a case where perspiration is performed for a given time; thereafter, the perspiration stops; and the perspiration is performed again, caused is a problem in that electrolyte ions generated upon the previous perspiration are dried, the dried electrolyte ions are fixed on a sensor part as salt, and the salt dissolves again upon the perspiration performed again, thereby exerting influence on measurement.

CITATION LIST

Non-Patent Literature

Non-Patent Literature 1: Wei Gao, et al., "Fully integrated wearable sensor arrays for multiplexed in situ perspiration analysis", Nature, Vol. 529, pp. 509-526, 2016.

SUMMARY

Technical Problem

In order to solve the above-mentioned problem, embodiments of the present invention have been devised, and objects of embodiments of the present invention are to provide a wearable sensor and a perspiration analysis device, each of which reduces influence exerted on analysis of components due to drying of perspiration and can realize analysis of the components in the perspiration for a long time.

Means for Solving the Problem

A wearable sensor of embodiments of the present invention includes: a base member which is worn on a body of a wearer; a hole-like flow passage which penetrates through the base member; a first sensor part which is configured to detect a signal as to electrical characteristics of a solution inside the flow passage; and a heater which is located in the base member in such a way as to enclose the flow passage.

In addition, in one configuration example of the wearable sensor of embodiments of the present invention, the base member is worn on the body of the wearer in such a way as to face skin of the wearer, the flow passage penetrates through the base member and an opening of the flow passage on one side is formed in such a way as to face the skin of the wearer, the first sensor part is located inside the flow passage and detects an electrical signal originating from an analysis target component in perspiration which is secreted from the skin of the wearer and flows into the flow passage, the heater is located in the base member in such a way as to enclose the flow passage from a periphery of the opening of the flow passage on a side of the skin to a position of a first sensor part inside the flow passage, and at least an inner wall of the flow passage has hydrophilia.

In addition, in the one configuration example of the wearable sensor of embodiments of the present invention, the wearable sensor further includes a water-repellent part which is provided on a surface of the base member on the side of the skin.

In addition, in the one configuration example of the wearable sensor of embodiments of the present invention, the wearable sensor further includes a porous film or fiber which is provided on an opening of the flow passage on a side opposite to the side of the skin.

In addition, in the one configuration example of the wearable sensor of embodiments of the present invention, the wearable sensor further includes a second sensor part for detection of the perspiration, the second sensor part being located in a position inside the flow passage, the position neighboring the first sensor part.

In addition, a perspiration analysis device of embodiments of the present invention includes: a wearable sensor; a component concentration calculation part being configured to calculate a concentration of the analysis target component from an electrical signal which is detected by a first sensor part of the wearable sensor; and a power supply control part being configured to supply power to a heater of the wearable sensor and heat the heater, when acquisition of the concentration of the analysis target component has been finished.

In addition, in one configuration example of the perspiration analysis device of embodiments of the present invention, when a value of the concentration of the analysis target component has been stabilized, the power supply control part determines that the acquisition of the concentration of the analysis target component has been finished.

In addition, a perspiration analysis device of embodiments of the present invention includes: a wearable sensor; a component concentration calculation part being configured to calculate a concentration of the analysis target component from an electrical signal which is detected by a first sensor part of the wearable sensor; and a power supply control part being configured to supply power to a heater of the wearable sensor and heat the heater, when acquisition of the concentration of the analysis target component has been finished, and when the second sensor part detects that perspiration secreted from skin of the wearer has reached a position of the first sensor part, the power supply control part determines that the acquisition of the concentration of the analysis target component has been finished.

In addition, in one configuration example of the perspiration analysis device of embodiments of the present invention, the perspiration analysis device further includes a communication part being configured to transmit a value of the concentration of the analysis target component to an external device, the value being calculated by the component concentration calculation part.

Effects of Embodiments of the Invention

According to embodiments of the present invention, surface tension of perspiration can be adjusted by a size of a flow passage, a position of a first sensor part inside the flow passage, and hydrophilia of an inner wall of the flow passage due to a capillary phenomenon in such a way that the perspiration reaches a position of the first sensor part and the perspiration does not reach an opening of the flow passage on a side opposite to a side of skin. In addition, in embodiments of the present invention, by providing a heater, the heater is heated after acquisition of a concentration of an analysis target component in the perspiration, and the perspiration is moved to an opening on the side opposite to the side of the skin and can be vaporized. As a result, in embodiments of the present invention, for perspiration component analysis in a wearable form, fixation of salt onto a surface of the first sensor part can be reduced, and analysis of components in the perspiration for a long time can be realized.

BREIF DESCRIPTION OF THE DRAWINGS

FIG. 3 is a cross-sectional view showing a configuration of a wearable sensor of the perspiration analysis device according to the embodiment of the present invention.

FIG. 5 is a cross-sectional view showing a manner in which perspiration of a wearer rises in a flow passage in the embodiment of the present invention.

DETAILED DESCRIPTION OF ILLUSTRATIVE EMBODIMENTS

Figure 1:
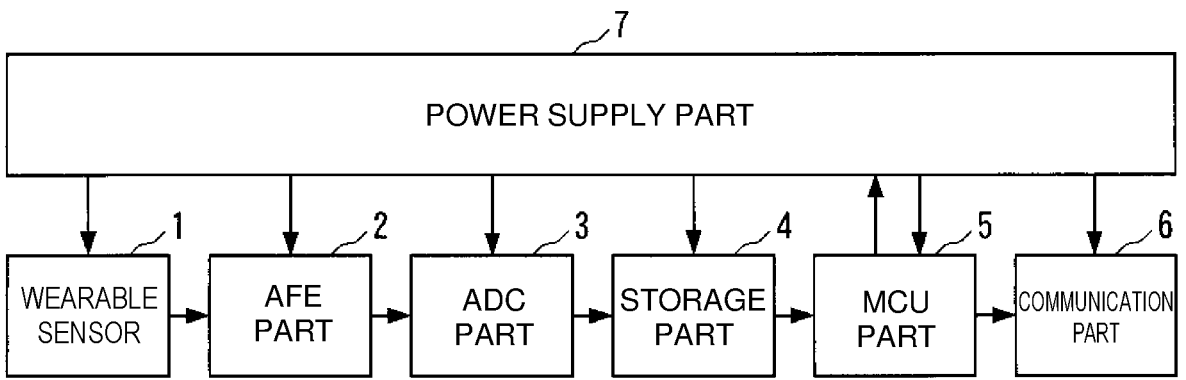
FIG. 1 is a block diagram showing a configuration of a perspiration analysis device according to an embodiment of the present invention.

Hereinafter, an embodiment of the present invention will be described with reference to the accompanying drawings. FIG. 1 is a block diagram showing a configuration of a perspiration analysis device according to the embodiment of the present invention. The perspiration analysis device includes a wearable sensor 1, an analog front end (AFE) part 2, an analog digital converter (ADC) part 3, a storage part 4, a micro control unit (MCU) part 5, a communication part 6, and a power supply part 7.

The wearable sensor 1 detects an electrical signal originating from an analysis target component in perspiration secreted from skin of a wearer.

The AFE part 2 includes an analog front end and amplifies a feeble electrical signal detected by the wearable sensor 1.

The ADC part 3 includes an analog-digital converter and converts an analog signal amplified by the AFE part 2 to digital data at a predetermined sampling frequency.

The storage part 4 stores the digital data outputted by the ADC part 3. The storage part 4 is realized by a non-volatile memory typified by a flash memory, a volatile memory such as a dynamic random access memory (DRAM), or the like.

The MCU part 5 is responsible for signal processing, in which a concentration of the analysis target component is calculated from the digital data stored in the storage part 4, and power supply control.

Figure 2:
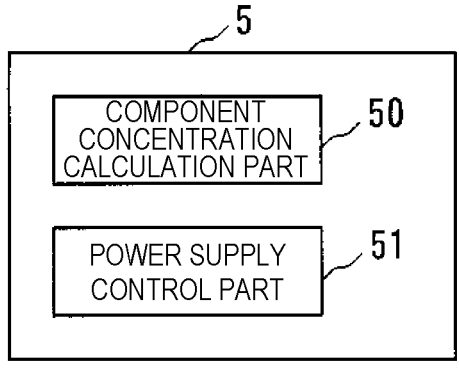
FIG. 2 is a functional block diagram of an MCU part of the perspiration analysis device according to the embodiment of the present invention.

FIG. 2 is a functional block diagram of the MCU part 5. The MCU part 5 functions as a component concentration calculation part 50 and a power supply control part 51.

The communication part 6 transmits an analysis result obtained by the MCU part 5 to an external device (not shown) such as a smartphone in a wireless or wired manner. As standards for wireless communication, for example, Bluetooth™ Low Energy (BLE) or the like is cited. In addition, as standards for wired communication, for example, Ethernet™ or the like is cited.

The power supply part 7 plays a role of supplying power to the perspiration analysis device.

Figure 3:
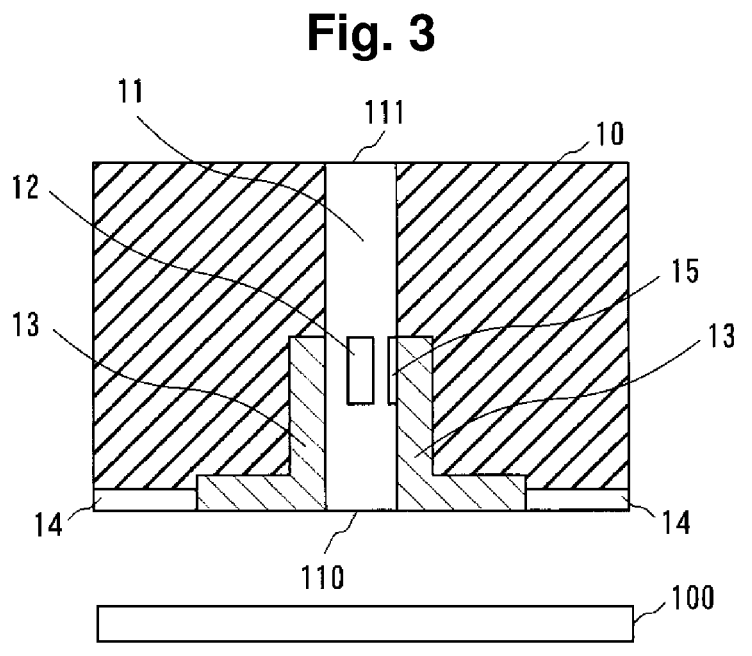

FIG. 3 is a cross-sectional view showing a configuration of the wearable sensor 1. The wearable sensor 1 includes a base member 10, a flow passage 11, a sensor part 12 (first sensor part), a heater 13, a water-repellent part 14, and a sensor part 15 (second sensor part). The base member 10 is worn on a body of the wearer in such a way as to face skin 100 of the wearer in the wearable sensor 1. The flow passage 11 penetrates through the base member 10 and is a hole-like flow passage formed in such a way that an opening no of the flow passage 11 on one side thereof faces the skin of the wearer. The sensor part 12 (first sensor part) is located inside the flow passage 11 and detects an electrical signal originating from an analysis target component in perspiration which is secreted from the skin 100 of the wearer and flows into the flow passage 11. The heater 13 is located in the base member 10 in such a way as to enclose the flow passage 11 from a periphery of the opening no of the flow passage 11 on a side of the skin 100 to a position of the sensor part 12 inside the flow passage 11. The water-repellent part 14 is provided on a surface of the base member 10 on the side of the skin 100. The sensor part 15 (second sensor part) is a sensor part for detecting the perspiration, which is located in a position inside the flow passage 11, the position neighboring the sensor part 12.

As the base member 10, for example, a base member formed of a hydrophile glass material or a base member formed of a hydrophile resin material is cited. In addition, the base member 10 may be a base member which is subjected to surface treatment which imparts hydrophilia to a surface of the water-repellent material and an inner wall of the flow passage 11. A diameter of the flow passage 11 formed in the base member 10 is, for example, approximately several mm.

In a case where a hydrophile material is used as a material of the base member 10, it is only required to form the water-repellent part 14 by conducting surface treatment which imparts water repellency to the surface (a lower surface in FIG. 3) of the base member 10 on the side of the skin 100. In a case where a water-repellent material is used as the material of the base member 10, surface treatment which imparts hydrophilia to a surface (an upper surface in FIG. 3) of the base member 10 on a side opposite to the side of the skin 100 and the inner wall of the flow passage 11 is conducted and only the surface of the base member 10 on the side of the skin 100 is made to remain the water-repellent material, thereby allowing this surface on the side of the skin 100 to be the water-repellent part 14.

As an example of the sensor part 12, an electrochemical sensor such as an ion selective electrode used in Non-Patent Literature 1, an enzyme electrode, an ion sensitive field-effect transistor can be cited.

The sensor part 12 is formed on, for example, an inner wall surface of the flow passage 11. Note that in order to analyze a plurality of components in the perspiration, a plurality of sensor parts 12, each of which has selectivity of a target component, may be provided.

The heater 13 is located in the base member 10 in such a way as to enclose the flow passage 11 from the periphery of the opening no of the flow passage 11 on the side of the skin 100 to the position of the sensor part 12 inside the flow passage 11. As the heater 13, for example, a metal heating element formed of platinum or the like, non-metal heating element formed of silicon carbide or the like, and a heating element of metal heating element or non-metal heating element whose surface is covered with, for example, a protective film of glass or the like are cited. As described later, power for the heater 13 is supplied from the power supply part 7.

Note that although in the example shown in FIG. 3, an example in which the heater 13 is exposed onto a surface of the base member 10 on the side of the skin 100 and a wall surface of the flow passage 11 is shown, by covering a surface of the heater 13 with hydrophile glass or hydrophile resin, a form of the heater 13, in which the heater 13 is not exposed to the surface of the base member 10 on the side of the skin 100 and the wall surface of the flow passage 11, may be adopted. In a case where the surface to which the heater 13 is exposed has water repellency, it is desirable that the surface of the heater 13 is covered with a hydrophile material so as to impart hydrophilia to at least the inner wall of the flow passage 11.

Figure 4:
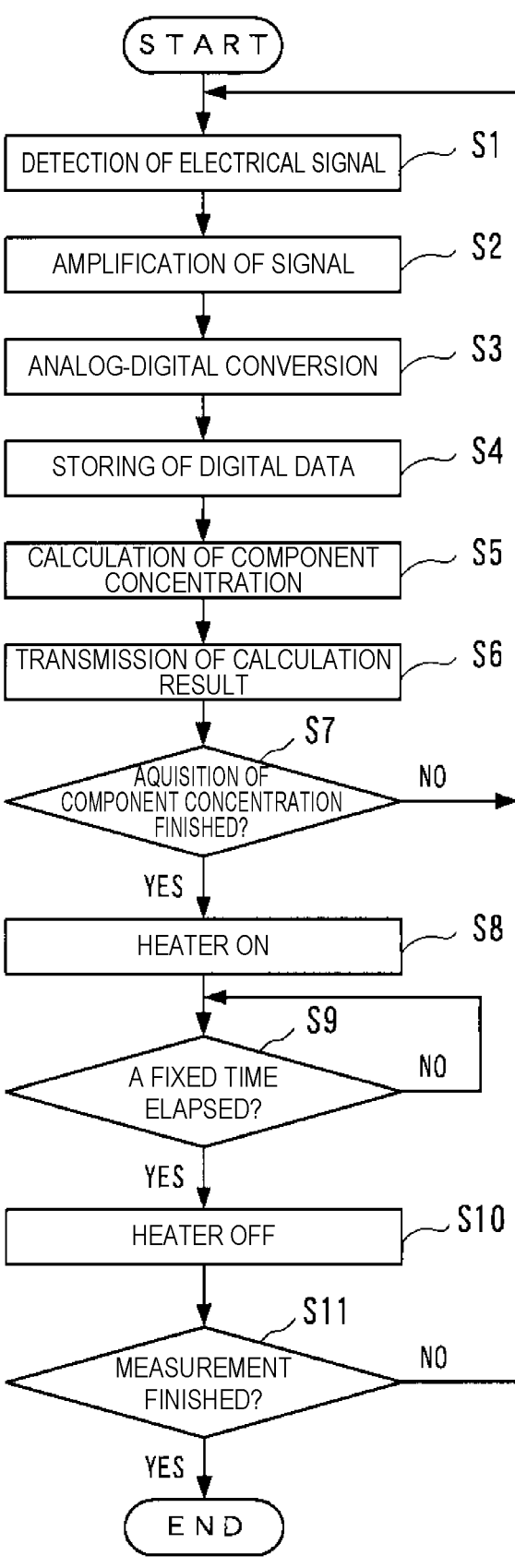
FIG. 4 is a flowchart for explaining operation of the perspiration analysis device according to the embodiment of the present invention.
Figure 5:
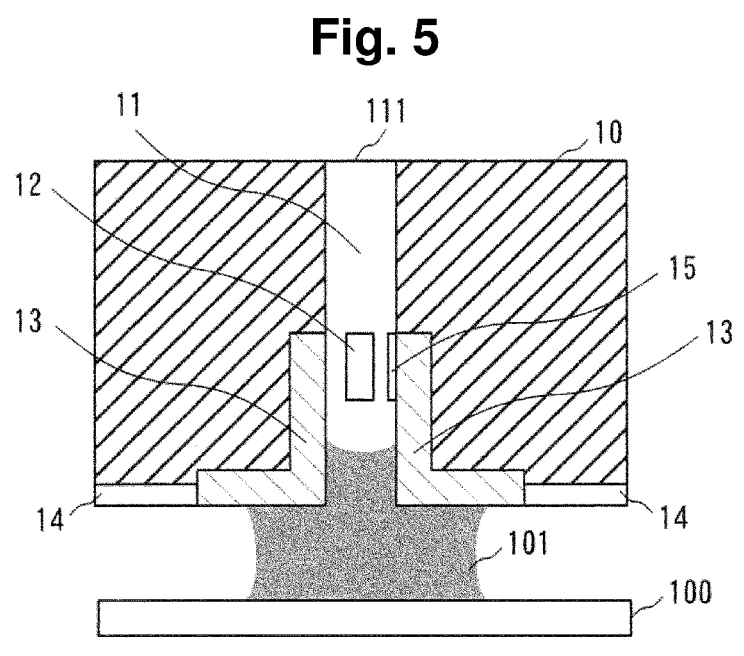
Figure 6:
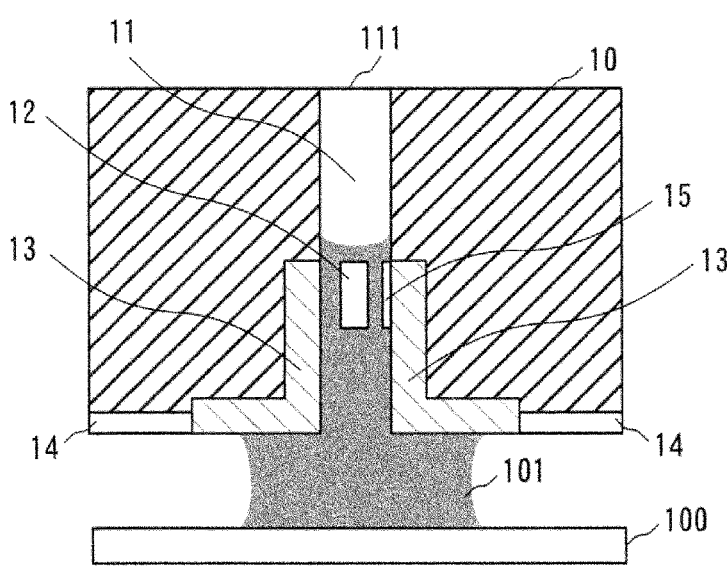
FIG. 6 is a cross-sectional view showing a manner in which rising in the flow passage, the perspiration of the wearer has reached a position of a sensor part in the embodiment of the present invention.

FIG. 4 is a flowchart for explaining operation of the perspiration analysis device of the present embodiment. Upon staring measurement, a liquid droplet of the perspiration is formed between the skin 100 of the wearer and the flow passage 11 by a capillary phenomenon and a hydrophilic/hydrophobic pattern of the flow passage 11 (a pattern in which the inner wall of the flow passage 11 is hydrophilic and the water-repellent part 14 on the periphery of the flow passage 11 is water-repellent). In accordance with an increase in a secretion amount of the perspiration, an interface between the perspiration and the air moves only inside the flow passage 11, and as shown in FIG. 5, the perspiration 101 is introduced into the flow passage 11. As shown in FIG.

6, the perspiration 101 reaches the position of the sensor part 12 inside the flow passage 11.

It is only required for the diameter of the passage 11, a length of the flow passage 11, the position of the sensor part 12 inside the flow passage 11, and hydrophilia (wettability) of the inner wall of the flow passage 11 to be set in such a way that the perspiration 101 reaches the position of the sensor part 12 due to the capillary phenomenon and the perspiration 101 does not reach the opening in of the flow passage 11 on the side opposite to the side of the skin 100.

The sensor part 12 detects the electrical signal originating from the analysis target component in the perspiration 101 (step S1 in FIG. 4).

The AFE part 2 amplifies the feeble electrical signal detected by the sensor part 12 (step S2 in FIG. 4).

The ADC part 3 converts the analog signal amplified by the AFE part 2 to the digital data (step S3 in FIG. 4). The digital data outputted from the ADC part 3 is stored in the storage part 4 (step S4 in FIG. 4).

The component concentration calculation part 50 calculates a concentration of the analysis target component from the digital data stored in the storage part 4 (step S5 in FIG. 4). As examples of component concentrations in the perspiration 101, for example, a lactic acid concentration, a glucose concentration, a sodium ion concentration, a potassium ion concentration, and the like are cited. Note that as is clear from Non-Patent Literature 1, since the technology for calculating the component concentration is well-known, detailed description therefor is omitted.

The communication part 6 transmits a value of the component concentration calculated by the component concentration calculation part 50 to the external device (not shown) such as a smartphone (step S6 in FIG. 4).

Next, for example, when the water detection sensor part 15 located in the position neighboring the position of the sensor part 12 inside the flow passage 11 detects that the perspiration 101 has reached the position of the sensor part 12, the power supply control part 51 determines that acquisition of the component concentration has been finished (YES in step S7 in FIG. 4).

Alternatively, when a change amount of the value of the component concentration calculated by the component concentration calculation part 50 per unit time is a predetermined threshold or less, the power supply control part 51 may determine that the value of the component concentration has been stabilized and may determine that the acquisition of the component concentration has been finished.

Figure 7:
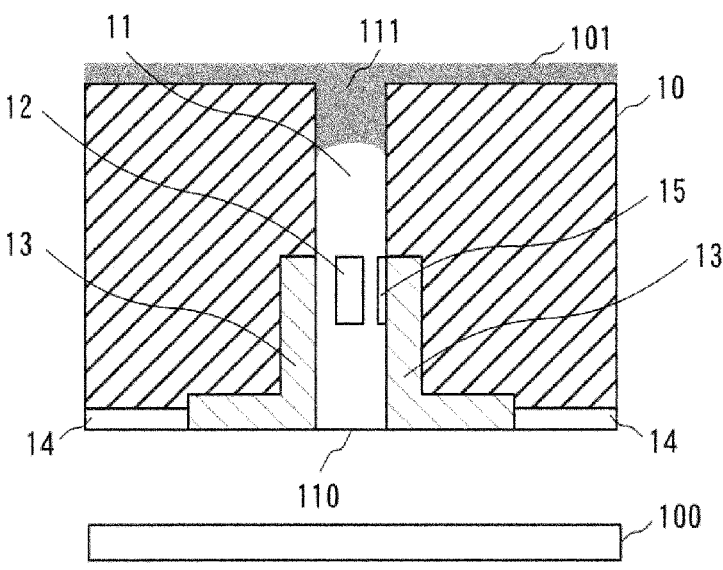
FIG. 7 is a cross-sectional view showing a manner in which the perspiration of the wearer moves to a side opposite to a side of skin in the embodiment of the present invention.

When the power supply control part 51 determines that the acquisition of the component concentration has been finished, the power supply control part 51 causes the power supply part 7 to supply power to the heater 13, thereby heating the heater 13 (step S8 in FIG. 4). When the position from the side of the skin of the flow passage 11 to the sensor part 12 is heated by heating of the heater 13 (heater ON) is heated, due to a thermocapillary phenomenon and Marangoni effect, the perspiration 101 moves in the flow passage 11 to the opening in (the opening 111 on the side opposite to the side of the skin 100) on a low temperature side on which the heater 13 is not provided and is vaporized from the opening in thereon and the surface of the base member 10 therearound (FIG. 7). In this way, the perspiration 101 can be eliminated from the wearable sensor 1.

Note that a porous film such as a membrane filter or fiber, which has high water absorbency and moisture desorption, such as rayon, silk, and cotton may be disposed in the opening 111. This makes it possible to increase an efficiency of the elimination and drying of the perspiration 101, whose component concentration has been measured, in the opening 111.

When a fixed time from a time point of starting supplying of the power to the heater 13 has elapsed (YES in step S9 in FIG. 4), the power supply control part 51 stops supplying of the power to the heater 13 (step S10 in FIG. 4). Introduction of the perspiration 101 into the flow passage 11 is resumed by stopping of heating of the heater 13 (heater OFF).

In this way, for example, until an instruction of finishing of measurement is issued from the wearer (YES in step S11 in FIG. 4), processing in steps S1 to S10 are repeatedly executed.

As described above, in the perspiration component analysis in a wearable form, fixation of salt to the surface of the sensor part 12 can be reduced and analysis of the components in the perspiration for a long time can be realized by the present embodiment. Although it is likely that salt originating from dried electrolyte ions is attached to the surface of the base member 10 on the periphery of the opening in of the flow passage 11, since the salt is located in the position which is separated from the skin 100 and the sensor part 12, likelihood with which the salt attached to the surface of the base member 10 dissolves upon perspiring again and reaches the sensor part 12 is low.

In addition, in the present embodiment, when a volume of liquid droplets of the perspiration 101 generated between the skin 100 of the wearer and the flow passage 11 and a surface area of the wearable sensor 1, which contacts these liquid droplets, can be previously estimated, a perspiration speed and a cumulative perspiration amount of the wearer per unit area can be calculated.

In other words, each time the heater 13 is turned ON, by adding the above-mentioned already-known volume, the component concentration calculation part 50 can calculate the cumulative perspiration amount of the wearer in a total of elapsed times from heater OFF to the next heater ON.

In addition, each time the heater 13 is turned ON, by dividing the above-mentioned already-known volume by an elapsed time from the immediately previous heater OFF to the heater ON and the above-mentioned surface area, the component concentration calculation part 50 can calculate the perspiration speed of the wearer per unit area.

Figure 8:
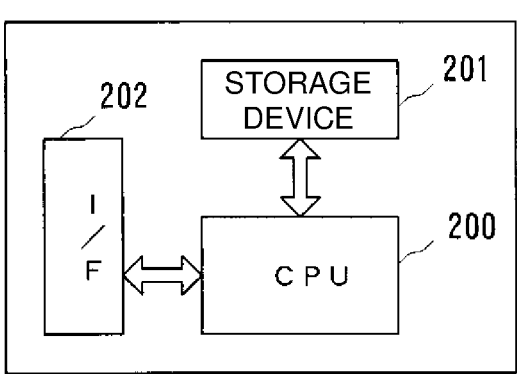
FIG. 8 is a block diagram showing a configuration example of a computer which realizes the perspiration analysis device according to the embodiment of the present invention.

The storage part 4 and the MCU part 5 descried in the present embodiment are realized by a computer, which includes a central processing unit (CPU), a storage device, and an interface, and programs which control these hardware resources. A configuration example of this computer is shown in FIG. 8. The computer includes a CPU 200, a storage device 201, and an interface device (hereinafter, abbreviated as an I/F) 202. The ADC part 3, the communication part 6, the power supply part 7, and the like are connected to the I/F 202. In such a computer, the programs for realizing a perspiration analysis method of embodiments of the present invention are stored in the storage device 201. In accordance with the programs stored in the storage device 201, the CPU 200 executes the processing described in the present embodiment.

INDUSTRIAL APPLICABILITY

Embodiments of the present invention are applicable to technology which analyzes components in perspiration of a human being.

REFERENCE SIGNS LIST

1 Wearable sensor
2 AFE part

3 ADC part
4 Storage part
5 MCU part
6 Communication part
7 Power supply part
10 Base member
11 Flow passage
12 Sensor part
13 Heater
14 Water-repellent part
15 Water detection sensor part
50 Component concentration calculation part
51 Power supply control part
100 Skin
101 Perspiration
110, 111 Opening.

The invention claimed is:

1. A wearable sensor comprising:
a base member configured to be worn on a body of a wearer;
a flow passage which penetrates through the base member;
a first sensor part configured to detect a signal as to electrical characteristics of perspiration inside the flow passage; and
a heater which is located in the base member, wherein the heater encloses the flow passage, wherein the heater is configured to cause the perspiration to move away from the first sensor part to an opening of the flow passage that is opposite to the body of the wearer, wherein the heater surrounds the first sensor part.

2. The wearable sensor according to claim 1, wherein:
the base member is configured to face skin of the wearer;
a first opening of the flow passage is configured to face the skin of the wearer;
the first sensor part is configured to detect an electrical signal originating from an analysis target component in perspiration that is secreted from the skin of the wearer and flows into the flow passage;
the heater encloses the flow passage from a periphery of the first opening to a position of a first sensor part inside the flow passage; and
at least an inner wall of the flow passage is hydrophilic.

3. The wearable sensor according to claim 2, further comprising a water-repellent part on a surface of the base member on a side of the skin.

4. The wearable sensor according to claim 2, further comprising a porous film or fiber on a second opening of the flow passage, wherein the second opening of the flow passage is configured to be opposite to the skin.

5. The wearable sensor according to claim 2, further comprising a second sensor part for detection of the perspiration that is secreted from the skin of the wearer and flows into the flow passage, the second sensor part being located in a position inside the flow passage neighboring the first sensor part.

6. A perspiration analysis device comprising:
a wearable sensor comprising:
a base member configured to be worn on a body of a wearer;
a flow passage which penetrates through the base member;
a first sensor part configured to detect a signal as to electrical characteristics of perspiration inside the flow passage; and a heater which is located in the base member, wherein the heater encloses the flow passage, wherein the heater surrounds the first sensor part;

a component concentration calculation part configured to calculate a concentration of an analysis target component from an electrical signal which is detected by the first sensor part; and a power supply control part configured to supply power to the heater and heat the heater in response to determining that acquisition of the concentration of the analysis target component has been finished to move the perspiration away from the first sensor part to an opening of the flow passage that is opposite to the body of the wearer.

7. The perspiration analysis device according to claim 6, wherein when a value of the concentration of the analysis target component has been stabilized, the power supply control part determines that the acquisition of the concentration of the analysis target component has been finished.

8. The perspiration analysis device according to claim 7 further comprising a communication part configured to transmit a value of the concentration of the analysis target component to an external device, the value being calculated by the component concentration calculation part.

9. A perspiration analysis device comprising:

a wearable sensor comprising:

a base member configured to be worn on a body of a wearer and to face skin of the wearer;

a flow passage which penetrates through the base member, wherein a first opening of the flow passage is configured to face the skin of the wearer;

a first sensor part configured to detect an electrical signal originating from an analysis target component in perspiration that is secreted from the skin of the wearer and flows into the flow passage;

a heater which is located in the base member, wherein the heater encloses the flow passage from a periphery of the first opening to a position of the first sensor part inside the flow passage; and a second sensor part for detection of the perspiration that is secreted from skin of the wearer and flows into the flow passage, the second sensor part being located in a position inside the flow passage neighboring the first sensor part, wherein at least an inner wall of the flow passage is hydrophilic;

a component concentration calculation part configured to calculate a concentration of the analysis target component from an electrical signal which is detected by the first sensor part; and a power supply control part configured to supply power to the heater and heat the heater in response to determining that acquisition of the concentration of the analysis target component has been finished to move the perspiration away from the first sensor part to an opening of the flow passage that is opposite to the body of the wearer, wherein when the second sensor part detects that the perspiration secreted from the skin of the wearer has reached a position of the first sensor part, the power supply control part determines that the acquisition of the concentration of the analysis target component has been finished.

10. The perspiration analysis device according to claim 9 further comprising a communication part configured to transmit a value of the concentration of the analysis target component to an external device, the value being calculated by the component concentration calculation part.

11. The wearable sensor according to claim 1, wherein the perspiration is vaporized from the opening of the flow passage that is opposite to the body of the wearer.

12. The wearable sensor according to claim 1, wherein the heater comprises at least one of a metal heating element formed of platinum or a non-metal heating element formed of silicon carbide.

13. The wearable sensor according to claim 1, wherein the first sensor part comprises at least one of an ion selective electrode, an enzyme electrode, or an ion sensitive field-effect transistor.

14. The wearable sensor according to claim 1, wherein the first sensor part is configured to detect at least one analysis target component selected from the group consisting of: lactic acid, glucose, sodium ions, and potassium ions.

15. The wearable sensor according to claim 1, wherein the base member comprises at least one of a hydrophilic glass material or a hydrophilic resin material.

16. The perspiration analysis device according to claim 6, wherein the power supply control part is configured to:

supply power to the heater for a fixed time period; and stop supplying power to the heater after the fixed time period has elapsed.

17. The perspiration analysis device according to claim 6, wherein the component concentration calculation part is further configured to calculate at least one of: a perspiration speed of the wearer per unit area, or a cumulative perspiration amount of the wearer.

18. The perspiration analysis device according to claim 6, wherein the heater is configured to cause the solution to move away from the first sensor part to the opening via at least one of thermocapillary action or Marangoni effect.

19. The perspiration analysis device according to claim 8, wherein the communication part is configured to transmit wirelessly using Bluetooth Low Energy.

20. The perspiration analysis device according to claim 9, wherein the second sensor part comprises a water detection sensor.

* * * * *